United States Patent [19]

Nyéki et al.

[11] 4,388,304
[45] Jun. 14, 1983

[54] ANGIOTENSIN-II ANALOGUES WITH ANTAGONIZING EFFECTS, CONTAINING AN ESTER GROUP IN POSITION 8, AND A PROCESS FOR THE PREPARATION THEREOF

[75] Inventors: Olga Nyéki; Lajos Kisfaludy; Egon Karpáti; Laszlo Szporny, all of Budapest, Hungary

[73] Assignee: Richter Gedeon Vegyeszeti Gyar RT, Budapest, Hungary

[21] Appl. No.: 225,048

[22] Filed: Jan. 14, 1981

[30] Foreign Application Priority Data

Jan. 18, 1980 [HU] Hungary .............................. 101/80

[51] Int. Cl.³ ...................... A61K 37/00; C07C 103/52
[52] U.S. Cl. ............................... 424/177; 260/112.5 R
[58] Field of Search ................... 260/112.5 R; 424/177

[56] References Cited

U.S. PATENT DOCUMENTS 3,907,762 9/1975 Regoli et al. ................. 260/112.5 R
3,973,006 8/1976 Ondetti ......................... 260/112.5 R
3,975,365 8/1976 Mazur .......................... 260/112.5 R

*Primary Examiner*—Delbert R. Phillips
*Attorney, Agent, or Firm*—Karl F. Ross; Herbert Dubno

[57] ABSTRACT

New octapeptides of the general formula (I),

X—Arg—Val—Tyr—Ile—His—Pro—Y—OA    (I)

wherein
  X stands for the acyl group of an N-methylamino acid or the acyl group of an aliphatic α-hydroxy- or α-aminooxycarboxylic acid,
  Y is the residue of an aliphatic amino acid, and
  A is a $C_{1-5}$ alkyl group, are prepared so that the protecting groups of a protected octapeptide derivative of the general formula (II),

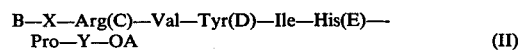

B—X—Arg(C)—Val—Tyr(D)—Ile—His(E)—Pro—Y—OA    (II)

wherein
  B is a group removable by acidolysis or catalytic hydrogenation,
  C is a group for the temporary protection of the guanidino group on the Arg moiety,
  D is a group for the temporary protection of the aromatic hydroxy group on the Tyr moiety,
  E is a group for the temporary protection of the imidazole group on the His moiety, and
  A, X and Y are as defined above, are removed either stepwise or in a single step. If desired, a compound of the general formula (I) is converted into its acid addition salt or pharmaceutically acceptable complex.

The new compounds according to the invention possess angiotensin-II antagonizing effects, and can be used in the therapy to diagnose or treat hypertensive states.

5 Claims, No Drawings

ANGIOTENSIN-II ANALOGUES WITH ANTAGONIZING EFFECTS, CONTAINING AN ESTER GROUP IN POSITION 8, AND A PROCESS FOR THE PREPARATION THEREOF

The invention relates to new peptides with angiotensin-II antagonizing effects, to pharmaceutical compositions containing them, as well as to a process for the preparation thereof.

The new compounds according to the invention correspond to the formula (I),

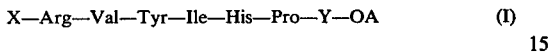

wherein
X stands for the acyl group of an N-methylamino acid, preferably sarcosyl group, or the acyl group of an aliphatic α-hydroxy- or α-aminooxycarboxylic acid,
Y is the residue of an aliphatic amino acid, and
A is a $C_{1-5}$ alkyl group.

The acid addition salts and complexes of the above peptides are also embraced by the scope of the invention.

The first angiotensin-II analog, which proved to be a specific competitive inhibitor of angiotensin-II under both in vitro and in vivo conditions, was described in 1970 [G. R. Marshal et al.: Proc. Natl. Acad. Sci. U.S.A. 67, 1624 (1970); P. A. Khairallah et al.: J. Med. Chem. 13, 181 (1970)]. This recognition initiated extensive research for the production of angiotensin-II analogs with antagonizing effects which may be applied to diagnose certain renine-dependent hypertensions and optionally in the treatment of such conditions, too. ($Sar^1$, $Ala^8$)-angiotensin-II, one of the many analogs with antagonizing effects prepared so far, has already been put on the market under the trade name Saralasin [D. T. Pals et al.: Circ. Res. 29, 673 (1971)]. Clinical tests performed with this compound proved that the substance is applicable for the diagnosis of hypertension of various origins [G. Bönner et al.: Dtsch. Med. Wschr. 104, 432 (1979)], as well as in the treatment of such conditions [J. L. Marx: Science 104, 821 (1976)]. It was also found that substances with angiotensin-II antagonizing effects can be used in the treatment of cardiac insufficiency caused by renovascular hypertension [H. Gavras et al.: JAMA 238, 880 (1977)].

By studying the relationships between the structures and biological effects of the angiotensin-II analogs prepared so far, several pieces of information have been obtained on the interpretation of agonistic and antagonistic effects. The main goal of recent research work is to produce antagonistic substances with prolonged biological half lives, which are free of certain undesired side effects, such as initial agonistic effects.

Now it has been found that by replacing the phenylalanine moiety in position 8 of the angiotensin-II molecule with an aliphatic amino acid, introducing an N-methylamino acid or an α-hydroxy or α-aminooxy acid into position 1 of the molecule and esterifying the terminal carboxy group of the molecule with a $C_{1-5}$ alkyl group, new competitive inhibitors of angiotensin-II are obtained, which considerably decrease the artificially produced hypertension and are active even upon subcutaneous administration.

The new compounds of the formula (I)

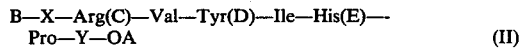

are prepared according to the invention such that the protecting groups of a protected octapeptide derivative of the formula (II), B—X—Arg(C)—Val—Tyr(D)—Ile—His(E)—Pro—Y—OA (II)

wherein
B is a group removable by acidolysis or catalytic hydrogenation, preferably a benzyloxycarbonyl group or a tert.-butoxycarbonyl group,
C is a group for the temporary protection of the guanidino group on the Arg moiety, preferably a nitro or a tosyl group,
D is a group for the temporary protection of the aromatic hydroxy group on the Tyr moiety, preferably a benzyl or a substituted benzyl group,
E is a group for the temporary protection of the imidazole group on the His moiety, preferably a dinitrophenyl group, and
A, X and Y are as defined above,
are removed either stepwise or in a single step. If desired, the resulting compounds of the formula (I) can be converted into their acid addition salts or complexes.

The octapeptide derivatives of the formula (II) used as starting substances in the process of the invention can be prepared by any method known in the peptide chemistry, e.g. as described in the Hungarian patent specification No. 168,431. When preparing the protected octapeptides, protecting groups which are stable under the conditions of acidolysis applied to remove the N-terminal protecting group after the coupling reaction should be utilized to protect the functional side groups.

According to a preferred method of the invention the protected octapeptide derivatives of the formula (II) are built up stepwise. One may also proceed so that a larger, appropriately protected peptide is used to acylate a smaller peptide or an amino acid. The peptides which contain an α-aminooxy acid in position 1 were synthesized by this latter method. In both instances groups which can be removed easily by acidolysis, e.g. a tert.-butoxycarbonyl group, can be used to protect temporarily the terminal amino groups of the individual amino acid derivatives. The protecting groups attached to the starting octapeptide derivative are split off preferably in a single step with liquid hydrogen fluoride or by catalytic hydrogenolysis, after removing the dinitrophenyl group by thiolysis. As catalyst e.g. palladium-on-carbon can be used.

If compounds of the formula (I) wherein X represents an aliphatic α-aminooxyacyl group are to be prepared, only acidolysis can be used to remove the protecting groups of the respective protected octapeptide ester of the formula (II) (the dinitrophenyl group is removed first and then the partially deprotected derivative is treated e.g. with hydrogen fluoride), since upon catalytic hydrogenation the amino group of the α-aminooxyacyl moiety would also split off, leading to the formation of a compound of the formula (I) wherein X is a α-hydroxyacyl moiety. This also means that compounds of the formula (I) wherein X is an aliphatic α-hydroxyacyl group can be prepared from the respective protected octapeptide esters of the formula (II) wherein X stands for an α-aminooxyacyl moiety, by subjecting the latter compounds to catalytic hydrogenation.

The compounds of the formula (I) are purified by methods known per se, preferably by ion exchange chromatography on carboxymethyl cellulose. The end product is separated from the effluent preferably by freeze drying to obtain a powdery substance which can be used directly in the preparation of various pharmaceutical compositions.

The antagonistic effects of the new compounds of the general formula (I) were investigated on narcotized male cats. After treating the animals with a ganglion blocking agent and bisecting the cervical vagus nerves on both side, an infusion of Hypertensin (CIBA) was given to the animals at a rate of 0.5 μg/kg/min. When the blood pressure of the animals reached a steady, increased level, the substance to be tested was administered either intravenously or subcutaneously in physiological saline solution or as an aqueous solution which also contained a carrier. The blood pressure drop was measured in mm Hg units, and the extent of decrease was expressed in percent related to the value before treatment. The statistical evaluation was performed on the basis of the blood pressure differences, by Student's single sample "t" test. The results are summarized in Table 1. The term "duration of effect" denotes the period elapsed until the observation of the last, still significant ($p=5\%$) blood pressure difference.

with an organic or mineral carrier applicable for enteral or parenteral administration. The pharmaceutical compositions may be e.g. freeze-dried solids containing carriers which do not react with the peptide, such as carbohydrates, or concentrated or dilute suspensions and emulsions which may also contain various preservatives and stabilizers.

The pharmaceutical compositions can be applied to diagnose and differentiate hypertensions of varying origin, and in the therapy to suppress hypertension of renal origin, to treat hypertensive crises, secondary cardiac insufficiency and other disturbances connected with hypertension.

The pharmaceutical compositions are presented preferably in the form of injections containing 1 to 10 mg of active agent. The active agents according to the invention can be used in daily doses of 1 to 10 mg for the treatment of adults. This amount is introduced preferably once a day in the form of an intravenous, subcutaneous or intramuscular injection or as a slow intravenous infusion.

The invention is elucidated in detail by the aid of the following non-limiting Examples.

The abbreviations used in the examples correspond to those generally applied in the literature [J. Biol. Chem. 247, 977 (1972)]. Further abbreviations are: HOAA=-

TABLE 1

Hypotensive effects of angiotensin-II analogs containing an ester group in position 8

| Analogues | i.v. | | | | s.c., phys. sal. | | | | s.c., CMC | | | | s.c., gelatine | | | |
|---|---|---|---|---|---|---|---|---|---|---|---|---|---|---|---|---|
| | d | n | % | m | d | n | % | m | d | n | % | m | d | n | % | m |
| ($Sar^1$,Ile—$OMe^8$)-Ang-II | 20 | 8 | 21 | 25 | 50 | 5 | 8 | 180 | 50 | 3 | 9 | φ | 100 | 8 | 5 | 15 |
| | 40 | 7 | 20 | 38 | 100 | 5 | 25 | 240 | 100 | 10 | 17 | 200 | 200 | 5 | 23 | 300 |
| ($Sar^1$,Ala—$OMe^8$)-Ang-II | 10 | 6 | 18 | 12 | 50 | 7 | 20 | 45 | 50 | 6 | 11 | 22 | | | | |
| | 20 | 9 | 29 | 60 | 100 | 8 | 20 | 45 | 100 | 7 | 18 | 22 | | | | |
| ($Sar^1$,Thr/Me/—$OMe^8$)-Ang-II | 20 | 7 | 12 | 12 | 100 | 5 | 27 | 45 | | | | | | | | |
| ($HOAA^1$,Ile—$OMe^8$)-Ang-II | 20 | 4 | 27 | 42 | 100 | 4 | 16 | 30 | | | | | | | | |
| Saralasin | 10 | 5 | 32 | 15 | 100 | 6 | 29 | 60 | 100 | 5 | 23 | 45 | 200 | 4 | 23 | φ |
| | | | | | 200 | 55 | 24 | 45 | 200 | 7 | 28 | 90 | | | | |

Remarks to Table 1:
d = dose,μg/kg
n = number of tests
m = duration of effect, minutes
phys. sal. = physiological saline solution
CMC = carboxymethyl cellulose It appears from the data of Table 1 that the angiotensin-II antagonistic compounds of the formula (I) examined possess significant hypotensive effects, which suggests the conclusion that the charge on the terminal carboxy group is not absolutely necessary to attain biological activity. The effect is significant even upon subcutaneous administration; when the compounds are administered in a solution which also contains a carrier, the duration of the effect may sometimes reach several hours.

The term "pharmaceutically acceptable complex" denotes compounds of the peptides of the formula (I) formed with certain organic or mineral substances which provide a protracted effect for the active agent. Of the organic complexing agents e.g. certain gelatines, carboxymethyl cellulose, alginates, polyflorethinephosphates, amino acid polymers and copolymers etc. are mentioned. As mineral complexing agents e.g. zinc hydroxide and poorly soluble zinc salts, such as zinc phosphates can be used.

The new peptides according to the invention and their pharmaceutically acceptable salts and complexes can be used in therapy in the form of pharmaceutical compositions. These compositions contain the new compounds according to the invention in admixture hydroxyacetic acid, OAla=α-aminooxypropionic acid, Pfp=pentafluorophenyl.

When preparing the compounds, evaporation was always performed on a Büchi-type Rotavapor apparatus. The melting points were measured with a Dr. Tottoli-type (Büchi) apparatus. The thin layer chromatograms were taken on a "Kieselgel-6" silica gel layer prepared according to Stahl, and the following solvent mixtures were used to develop the chromatograms:

(1) ethyl acetate:PAW=98:2
(2) ethyl acetate:PAW=95:5
(3) ethyl acetate:PAW=90:10
(4) ethyl acetate:PAW=80:20
(5) ethyl acetate:PAW=70:30
(6) ethyl acetate:PAW=60:40
(7) n-butanol:acetic acid:water=4:1:5.
(8) n-butanol:acetic acid:pyridine:water=30:6:20:24
(9) n-butanol:ethyl acetate:acetic acid:water=1:1:1:1
(10) ethyl acetate:PAW=75:25

PAW=a 20:6:11 mixture of pyridine, acetic acid and water

The thin layer chromatograms were visualized with ninhydrine or with chlorotolidine-potassium iodide.

The following general method was applied to purify the end products:

0.5 g of the free peptide are dissolved in 4 ml of a 0.01 molar ammonium acetate solution, and the solution is layered onto a column of 0.5 liters of carboxymethyl cellulose (CMC-52) equibrated previously with the same buffer solution. A gradient mixture of 1.5 liters of a 0.01 molar ammonium acetate solution of 1.5 liters of a 0.4 molar ammonium acetate solution is used as eluting agent. The eluting agent is passed through the column at a rate of 25 ml/hour, and the effluent is collected into fractions of 10 ml each. The composition of the effluent leaving the column is monitored continuously by an LKB Uvicord-II apparatus, the main fraction is separated on the basis of the curve obtained, and then freeze-dried in a Leybold-Hereus freeze-drier. If necessary, the product is subjected repeatedly to chromatography, by applying gradient elution again.

EXAMPLE 1

Preparation of (sarcosine[1], isoleucine methyl ester[8])angiotensin-II

STEP 1

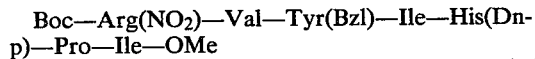

1.05 ml of triethyl amine and 1.90 g (5 mmoles) of Boc—Pro—OPfp are added to a solution of 1.36 g (7.5 mmoles) of Ile-OMe.HCl in 30 ml of chloroform. The solution is allowed to stand for 30 minutes under maintaining the pH at the initial value, then washed successively with water, 10% aqueous citric acid solution and with water again, dried and evaporated to dryness. The protected dipeptide, $R_f^{(1)}=0.8$, obtained as residue is dissolved in 5 ml of a 8 n solution of hydrochloric acid in dioxane, and after 15 minutes of standing 20 ml of dry ether are added to the solution. The mixture is evaporated, and the free dipeptide hydrochloride, $R_f^{(5)}=0.46$, is dissolved immediately in 30 ml of chloroform. The pH of the solution is adjusted to 8 with triethyl amine, and 4.36 g (7.5 mmoles) of Boc—His(Dnp)—OPfp are added. The solution is allowed to stand for one hour under maintaining the pH at the initial value, then 0.83 ml of N,N-dimethylamino-ethylamine are added. The mixture is allowed to stand for 10 minutes, then washed successively with 10% aqueous citric acid solution saturated with sodium chloride, 1 n aqueous hydrochloric acid, 5% aqueous sodium hydrocarbonate solution and water, dried and evaporated to dryness. The resulting protected tripeptide, $R_f^{(2)}=0.45$, is dissolved directly in 10 ml of a 8 n hydrochloric acid solution in dioxane, the solution is allowed to stand for 15 minutes, and then the free tripeptide hydrochloride, $R_f^{(5)}=0.30$, is precipitated with dry ether. The substance is filtered off, washed, and dissolved immediately in 15 ml of dimethyl formamide. The pH of the solution is adjusted to 8, and 2.4 g (6 mmoles) of Boc—Ile—OPfp are added. The solution is allowed to stand for 30 minutes under maintaining the pH at the initial value, then the solvent is removed and the residue is dissolved in ethyl acetate. This solution is washed successively with 10% aqueous citric acid solution, 1 n aqueous hydrochloric acid and water, dried and evaporated. The residue is triturated with a 1:9 mixture of ether and n-hexane, and the solid is filtered off. The resulting protected tetrapeptide, $R_f^{(2)}=0.31$, is dissolved in 7 ml of a 8 n solution of hydrochloric acid in dioxane, the solution is allowed to stand for 15 minutes, and then the product is precipitated with dry ether and filtered off. The resulting free tetrapeptide hydrochloride, $R_f^{(5)}=0.38$, is dissolved in a mixture of 20 ml of chloroform and 10 ml of dimethyl formamide, the pH of the solution is adjusted to 8, and 2.96 g (5.5 mmoles) of Boc—Tyr(Bzl)—OPfp are added. The solution is allowed to stand for 15 minutes under maintaining the pH at the initial value, thereafter the solvent is evaporated, the residue is dissolved in ethyl acetate, and 0.22 ml of N,N-dimethylamino-ethylamine are added. The mixture is allowed to stand for 10 minutes, then washed successively with 10% aqueous citric acid solution, 1 n aqueous hydrochloric acid and water, dried and evaporated. The residue is triturated with dry ether, and the solid is filtered off. The resulting protected pentapeptide, $R_f^{(2)}=0.52$, is dissolved in 10 ml of a 8 n solution of hydrochloric acid in dioxane, the solution is allowed to stand for 15 minutes, and then the product is precipitated with dry ether. The solid is filtered off and washed. The resulting free pentapeptide hydrochloride, $R_f^{(5)}=0.8$, is dissolved immediately in 20 ml of dimethyl formamide, the pH of the solution is adjusted to 8, and 2.3 g (6 mmoles) of Boc—Val—OPfp are added. The solution is allowed to stand for one hour under maintaining the pH at the initial value, then the solvent is evaporated and the residue is dissolved in chloroform. This solution is washed successively with 10% aqueous citric acid solution, 1 n aqueous hydrochloric acid and water, dried and evaporated. The residue is triturated with dry ether, and the solid is filtered off. The resulting protected hexapeptide, $R_f^{(2)}=0.43$, is dissolved immediately in a 8 n solution of hydrochloric acid in dioxane, the solution is allowed to stand for 15 minutes, and the product is precipitated with dry ether. The solid is filtered off and washed. The resulting free hexapeptide hydrochloride is dissolved immediately in 15 ml of dimethyl formamide, the pH of the solution is adjusted to 8, and 2.6 g (6 mmoles) of Boc—Arg(NO₂)—OPfp are added. The solution is allowed to stand for 30 minutes under maintaining the pH at the initial value, thereafter 45 ml of chloroform are added, and the mixture is washed with 1 n aqueous hydrochloric acid and water. The mixture is dried, evaporated, the residue is triturated with ethyl acetate and filtered off. 3.3 g (51% calculated for Boc—Pro—OPfp, which corresponds to a yield of 90% in the individual steps) of the protected heptapeptide are obtained; $R_f^{(3)}=0.37$.

STEP 2

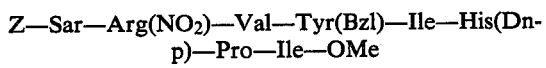

A solution of 3.3 g (2.5 mmoles) of Boc—Arg(NO₂)—Val—Tyr(Bzl)—Ile—His(Dnp)—Pro—Ile—OMe in 15 ml of a 8 n hydrochloric acid solution in dioxane is allowed to stand for 20 minutes, and then dry ether is added. The separated product is filtered off and washed. The resulting free heptapeptide hydrochloride, $R_f^{(5)}=0.7$, is dissolved immediately in 15 ml of dimethyl formamide. The pH of the solution is adjusted to 8, and 2.4 g (6 mmoles) of Z—Sar—OPfp are added. The solution is allowed to stand for 30 minutes under maintaining the pH at the initial value, then 45 ml of chloroform are added, and the solution is washed with 1 n aqueous hydrochloric acid and water. The solution is dried, evaporated, the residue is triturated with ethanol, and the solid is filtered off. 3.17 g (89%) of the protected octapeptide are obtained; $R_f^{(4)}=0.82$, m.p.: 197°–209° C.

STEP 3

Removal of the protecting groups 4.6 ml of 2-mercaptoethanol are added to a solution of 2.59 g (1.83 mmoles) of Z—Sar—Arg(NO$_2$)—Val—Tyr(Bzl)—Ile—His(Dnp)—Pro—Ile—OMe, the mixture is stirred for 1.5 hours, thereafter the product is precipitated with dry ether and filtered off. 2.0 g (87%) of the partially deprotected peptide, not containing dinitrophenyl group, are obtained; $R_f^{(4)}=0.42$. This protected octapeptide is dissolved in 40 ml of a 5:1:1 mixture of methanol, acetic acid and water, 1.0 g of a 10% palladium-on-carbon catalyst is added, and hydrogen is bubbled through the mixture for 20 hours under vigorous stirring. At the end of the reaction the catalyst is filtered off, washed with the above solvent mixture, the filtrate and the wash are combined and evaporated to dryness. The residue is admixed with aqueous ethanol, and the mixture is evaporated. This operation is repeated several times. Finally the residue is triturated with dry ether, filtered off and dried. 1.56 g (98%) of the free octapeptide methyl ester are obtained.

STEP 4

The crude free octapeptide methyl ester obtained in Step 3 is purified according to the general procedure described above. The physical constants of the resulting (sarcosine[1], isoleucine methyl ester[8])-angiotensin-II are as follows: Chromatographic characteristics: $R_f^{(7)}=0.19$, $R_f^{(8)}=0.59$, $R_f^{(9)}=0.38$. $E_{Glu}$ (pH=1.9): 1.00. Amino acid analysis: Pro 1.07 (1), Val 1.1 (1), Tyr 0.8 (1), His 1.03 (1), Arg 1.0 (1), Ile 1.87 (2), Sar 1.0 (1).

EXAMPLE 2

Preparation of (hydroxyacetyl[1], isoleucine methyl ester[8])-angiotensin-II

STEP 1

Z—OGly—Arg(NO$_2$)—Val—Tyr(Bzl)—Ile—His(Dnp)—Pro—Ile—OMe

A solution of 1.5 g (0.8 mmoles) of Boc—Arg(NO$_2$)—Val—Tyr(Bzl)—Ile—His(Dnp)—Pro—Ile—OMe, prepared as described in Step 1 of Example 1, in 6 ml of a 8 n hydrochloric acid solution in dioxane is allowed to stand for 20 minutes, and then the product is precipitated with dry ether. The resulting free heptapeptide hydrochloride, $R_f^{(5)}=0.7$, is washed and then dissolved immediately in 10 ml of dimethyl formamide. The pH of the solution is adjusted to 8 with triethyl amine, and 0.46 g (1.17 mmoles) of Z—OGly—OPfp are added. The mixture is allowed to stand for 30 minutes, then diluted with 30 ml of chloroform, washed successively with 10% aqueous citric acid solution, 1 n aqueous hydrochloric acid and water, dried and evaporated. The residue is triturated with ether, and the solid is filtered off. 1.05 g (93%) of the protected octapeptide are obtained; $R_f^{(3)}=0.24$, m.p.: 140°–145° C.

STEP 2

Removal of the protecting groups 2.3 ml of 2-mercaptoethanol are added to a solution of 1.05 g (0.74 mmoles) of Z—OGly—Arg(NO$_2$)—Val—Tyr(Bzl)—Ile—His(Dnp)—Pro—Ile—OMe in 5 ml of dimethyl formamide. The mixture is allowed to stand for 1.5 hours, then dry ether is added, and the precipitated product is filtered off and washed. 0.85 g (85%) of the partially deprotected octapeptide, containing no dinitrophenyl group, are obtained; $R_f^{(4)}=0.40$. 0.75 g (0.6 mmoles) of this protected octapeptide are dissolved in 20 ml of a 5:1:1 mixture of methanol, acetic acid and water, 0.8 g of a 10% palladium-on-carbon catalyst are added to the solution, and hydrogen is bubbled through the mixture for 18 hours under vigorous stirring. At the end of the reaction the catalyst is filtered off, washed with the above solvent mixture, the filtrate and the wash are combined and evaporated to dryness. Aqueous ethanol is added to the residue, and the mixture is evaporated. This operation is repeated several times, thereafter the residue is triturated with dry ether, filtered off and dried. 0.48 g (82%) of the free octapeptide methyl ester are obtained.

STEP 3

The crude octapeptide methyl ester obtained in Step 2 is purified according to the general procedure described above. The physical contents of the resulting product are as follows: Chromatographic characteristics: $R_f^{(7)}=0.29$, $R_f^{(8)}=0.72$, $R_f^{(9)}=0.60$. $E_{Glu}$ (pH=1.9): 0.60. Amino acid analysis: Pro 1.0 (1), Val 1.0 (1), Ile 1.7 (2), Tyr 0.88 (1), His 1.02 (1), Arg 0.96 (1).

EXAMPLE 3

Preparation of (L-α-aminooxypropionic acid[1], isoleucine methyl ester[8])-angiotensin-II

STEP 1

Boc—Arg(Tos)—Val—Tyr(Bzl)—Ile—His(Dnp)—Pro—OBzl 1.68 ml of triethyl amine and 5.87 g (10 mmoles) of Boc—His(Dnp)—OPfp are added to a solution of 2.9 g (12 mmoles) of Pro—OBzl.HCl in 50 ml of chloroform. The solution is stirred for one hour under maintaining the pH at the initial value, washed successively with 25 ml of a 10% aqueous citric acid solution, 1 n aqueous hydrochloric acid, 5% aqueous sodium hydrocarbonate solution and water, dried and evaporated. The residue is triturated with n-hexane, and the solid is filtered off. The resulting protected dipeptide, $R_f^{(3)}=0.80$, is dissolved in 13 ml of a 8 n hydrochloric acid solution in dioxane, the solution is allowed to stand for 15 minutes, and then the product is precipitated with dry ether. The free dipeptide hydrochloride, $R_f^{(4)}=0.24$, is filtered off, washed, and dissolved immediately in 30 ml of dimethyl formamide. The pH of the solution is adjusted to 8 with triethyl amine, and 4.7 g (12 mmoles) of Boc—Ile—OPfp are added. The solution is allowed to stand for one hour under maintaining the pH at the initial value, thereafter the solvent is evaporated, the residue is dissolved in chloroform, and the solution is washed successively with 10% aqueous citric acid solution, 1 n aqueous hydrochloric acid, 5% aqueous sodium hydrocarbonate solution and water. The solution is dried, evaporated, the residue is triturated with a 1:2 mixture of ether and n-hexane, and the solid is filtered off. The resulting protected tripeptide, $R_f^{(3)}=0.82$, is dissolved in 15 ml of a 8 n hydrochloric acid solution in dioxane, and after 15 minutes of standing the product is precipitated with dry ether. The free tripeptide hydrochloride, $R_f^{(5)}=0.38$, is filtered off, washed, and dissolved immediately in 50 ml of dimethyl formamide. The pH of the solution is adjusted to 8, 5.9 g (11 mmoles) of Boc—Tyr(Bzl)—OPfp are added, and the solution is allowed to stand for 30 minutes under maintaining the pH at the initial value. The solvent is evaporated, the residue is dissolved in ethyl acetate, and 0.22 ml of N,N-dimethylaminoethylamine are added. After 15 minutes of standing the mixture is washed successively with 10% aqueous citric acid solution, 1 n aqueous hydrochloric acid and water, dried and evaporated. The residue is triturated with ether and filtered. The resulting protected tetrapeptide, $R_f^{(3)}=0.73$, is dissolved immediately in 20 ml of a 8 n hydrochloric acid solution in dioxane, the solution is allowed to stand for 15 minutes, then the product is precipitated with dry ether, filtered off and washed. The resulting free tetrapeptide hydrochloride, $R_f^{(5)}=0.69$, is dissolved immediately in 50 ml of dimethyl formamide, the pH of the solution is adjusted to 8, and 4.2 g (11 mmoles) of Boc—Val—OPfp are added. The solution is allowed to stand for one hour under maintaining the pH at the initial value, thereafter the solvent is evaporated and the residue is dissolved in ethyl acetate. This solution is washed as described above, dried and evaporated. The residue is treated with n-hexane and then with dry ether, and the solid is filtered off. The resulting protected pentapeptide, $R_f^{(3)}=0.65$, is dissolved in 20 ml of a 8 n hydrochloric acid solution in dioxane. After 15 minutes of standing the product is precipitated with dry ether, filtered off and washed. The resulting free pentapeptide hydrochloride, $R_f^{(5)}=0.57$, is dissolved immediately in 60 ml of dimethyl formamide, the pH of the solution is adjusted to 8, and 5.94 g (10 mmoles) of Boc—Arg(Tos)—OPfp are added. The solution is allowed to stand for one hour under maintaining the pH at the initial value, and then the solvent is evaporated. The residue is dissolved in chloroform, the solution is washed successively with 10% aqueous citric acid solution, 1 n aqueous hydrochloric acid, 5% aqueous sodium hydrocarbonate solution and water, dried and evaporated. The residue is triturated with dry ether, and the solid is filtered off. 5.8 g (42% calculated for His, which corresponds to a yield of 84% in the individual steps) of Boc—Arg(Tos)—Val—Tyr(Bzl)—Ile—His(Dnp)—Pro—OBzl are obtained; $R_f^{(3)}=0.63$, m.p.: 167°–174° C.

STEP 2

Boc—Arg(Tos)—Val—Tyr(Bzl)—Ile—His—Pro—OH 2.8 g (2.1 mmoles) of the protected hexapeptide obtained as described in Step 1 of Example 3 are dissolved in 8 ml of dimethyl formamide. 2.9 ml of 2-mercaptoethanol are added, the solution is stirred for one hour, and then the product free of dinitrophenyl group is precipitated with dry ether. The resulting substance, $R_f^{(4)}=0.17$, is suspended in 30 ml of dioxane, and 12 ml of 1 n aqueous sodium hydroxide solution are added. After one hour of standing a clear solution is obtained. The pH of the solution is adjusted to 7 with 1 n aqueous hydrochloric acid, and dioxane is evaporated. The pH of the aqueous solution obtained as residue is adjusted to 3, and 60 ml of a 2:3 mixture of dimethyl formamide and chloroform are added to the acidic mixture in order to dissolve the precipitate. The organic solution is separated from the aqueous phase, and the solvents are evaporated. 2.3 g (96%) of the hexapeptide are obtained; $R_f^{(5)}=0.37$, m.p.: 160°–164° C. (under decomposition).

STEP 3

Boc—Arg(Tos)—Val—Tyr(Bzl)—Ile—His—Pro—Ile—OMe 1.25 g (1.1 mmoles) of the hexapeptide prepared as described in Step 2 of Example 3 are dissolved in 15 ml of dimethyl formamide, and 0.5 ml (3.6 mmoles) of triethylamine, 0.65 g (3.6 mmoles) of Ile—OMe.HCl and 1.35 g (2 mmoles) of a crystalline complex of dicyclohexyl carbodiimide and pentafluorophonol containing the two compounds in a ratio of 1:3 are added to the solution. The mixture is allowed to stand at the initial pH value for 24 hours, then 0.65 g of Ile—OMe.HCl and 1.35 g of the above complex are added. After additional 24 hours the reaction mixture is diluted with 45 ml of chloroform and washed successively with 10% aqueous citric acid solution (2×20 ml), 5% aqueous sodium hydrocarbonate solution and water. The solution is dried, evaporated, and dry ether is added to the residue to separate the protected heptapeptide ester, $R_f^{(10)}=0.26$. The product is dissolved in 20 ml of hot ethanol, the solution is allowed to cool, and the product is filtered off. 0.95 g (65%) of Boc—Arg(Tos)—Val—Tyr(Bzl)—Ile—His—Pro—Ile—OMe are obtained.

STEP 4

Boc—L—OAla—Arg(Tos)—Val—Tyr(Bzl)—Ile—His—Pro—Ile—OMe 0.95 g (0.75 mmoles) of the protected heptapeptide ester prepared as described in Step 3 of Example 3 are dissolved in 3 ml of a 8 n hydrochloric acid solution in dioxane, and after 15 minutes of standing dry ether is added. The precipitated free heptapeptide ester hydrochloride, $R_f^{(5)}=0.24$, is filtered off, washed and dissolved immediately in 10 ml of dimethyl formamide. The pH of the solution is adjusted to 8, and 0.5 g (1.1 mmoles) of Boc—OAla—OPfp are added. The mixture is allowed to stand for one hour under maintaining the pH at the initial value, then diluted with 30 ml of chloroform and washed with a 10% aqueous citric acid solution and water. The solution is dried, evaporated, the residue is triturated with ether, and the solid is filtered off. 0.83 g (87%) of Boc—L—OAla—Arg(Tos)—Val—Tyr(Bzl)—Ile—His—Pro—Ile—OMe are obtained; m.p.: 143°–146° C. (under decomposition), $R_f^{(4)}=0.34$.

STEP 5

Removal of the protecting groups 0.75 g (0.57 mmoles) of the protected octapeptide ester prepared as described in Step 4 of Example 3 are dissolved in 2 ml of liquid hydrogen fluoride containing 0.5 ml of thioanisole. The reaction mixture is maintained at 0° C. for 1.5 hours, thereafter the free octapeptide is precipitated with dry ether. This product is dissolved in 30 ml of methanol and precipitated again with dry ether. 0.5 g (89%) of the crude free octapeptide ester are obtained.

STEP 6

The free octapeptide ester obtained as described in Step 5 of Example 3 is purified according to the general procedure given above. The physical constants of the resulting (L-α-aminooxypropionic acid[1], isoleucine methyl ester[8])-angiotensin-II are as follows: Chromatographic characteristics: $R_f^{(7)}=0.30$, $R_f^{(8)}=0.68$, $R_f^{(9)}=0.46$. Amino acid analysis: Pro 1.0 (1), Val 1.05 (1), Ile 2.0 (2), Tyr 0.73 (1), His 0.85 (1), Arg 0.97 (1).

EXAMPLE 4

Preparation of (sarcosine[1], threonine/Me/methyl ester[8])-angiotensin-II

STEP 1

Z—Sar—Arg(NO$_2$)—Val—Tyr(Bzl)—Ile—His(Dnp)—Pro—Thr(Me)—OMe 2.28 g (6 mmoles) of Boc—Pro—OPfp are added to a solution of 0.68 g (4.5 mmoles) of Thr(Me)—OMe in 10 ml of chloroform. The solution is allowed to stand for 30 minutes under maintaining its pH at 8, thereafter the solvent is evaporated, the residue is dissolved in ethyl acetate, and 0.22 ml of N,N-dimethylamino-ethylamine are added. After 15 minutes of standing the mixture is washed successively with 10% aqueous citric acid solution saturated with sodium chloride, 1 n aqueous hydrochloric acid and water, dried and evaporated. The resulting protected dipeptide, $R_f^{(2)}=0.76$, is dissolved directly in 3 ml of a 8 n hydrochloric acid solution in dioxane, the solution is alllowed to stand for 15 minutes, then diluted with dry ether and evaporated. The resulting free dipeptide hydrochloride, $R_f^{(4)}=0.18$, is dissolved immediately in 10 ml of dimethyl formamide, the pH of the solution is adjusted to 8, and 2.95 g (5 mmoles) of Boc—His(Dnp)—OPfp are added. The solution is allowed to stand for 30 minutes under maintaining its pH at the initial value, then the solvent is evaporated, the residue is dissolved in ethyl acetate, and 0.11 ml of N,N-dimethylaminoethylamine are added. After 10 minutes of standing the solution is washed successively with 10% aqueous citric acid solution saturated with sodium chloride and water, dried and evaporated. The resulting protected tripeptide, $R_f^{(2)}=0.47$, is dissolved immediately in 5 ml of a 8 n solution of hydrochloric acid in dioxane, and after 15 minutes of standing the product is precipitated with dry ether. The free tripeptide hydrochloride, $R_f^{(4)}=0.3$, is filtered off, washed, and dissolved immediately in 10 ml of dimethyl formamide. The pH of the solution is adjusted to 8, and 2.0 g (5 mmoles) of Boc—Ile—OPfp are added. The mixture is allowed to stand at the same pH value for 30 minutes, thereafter the solvent is evaporated, the residue is dissolved in ethyl acetate, and the solution is washed as described above. The solution is dried, evaporated, the residue is triturated with a 3:7 mixture of ether and n-hexane, and the protected tetrapeptide, $R_f^{(2)}=0.28$, is filtered off. The product is dissolved immediately in 7 ml of a 8 n hydrochloric acid solution in dioxane, and after 15 minutes of standing the free tetrapeptide hydrochloride, $R_f^{(5)}=0.27$, is precipitated with dry ether. The product is filtered off, washed, dissolved in 10 ml of dimethyl formamide, the pH of the solution is adjusted to 8, and 2.7 g (5 mmoles) of Boc—Tyr(Bzl)—OPfp are added. The solution is allowed to stand for 30 minutes under maintaining the pH at the initial value, thereafter the solvent is evaporated, the residue is dissolved in ethyl acetate, and 0.11 ml of N,N-dimethylamino-ethylamine are added. After 15 minutes of standing the solution is washed with a 10% aqueous citric acid solution saturated with sodium chloride and then with water, dried and evaporated. The residue is triturated with dry ether, the protected pentapeptide, $R_f^{(2)}=0.51$, is filtered off, and dissolved in 5 ml of a 8 n hydrochloric acid solution in dioxane. After 15 minutes of standing the free pentapeptide hydrochloride is precipitated with dry ether, filtered off, washed and dissolved in 20 ml of dimethyl formamide. (The $R_f$ value of the free pentapeptide hydrochloride is 0.48 in solvent mixture 5). The pH of the solution is adjusted to 8, and 1.9 g (5 mmoles) of Boc—Val—OPfp are added. The solution is allowed to stand for 30 minutes under maintaining the pH at the initial value, and then the solvent is evaporated. The residue is dissolved in chloroform, the solution is washed as described above, dried, evaporated, and the product is isolated with dry ether. The resulting protected hexapeptide, $R_f^{(2)}=0.44$, is dissolved in 10 ml of a 8 n hydrochloric acid solution in dioxane, and after 15 minutes of standing dry ether is added to the solution. The precipitated free hexapeptide hydrochloride, $R_f^{(4)}=0.36$, is filtered off, washed, and dissolved immediately in 15 ml of dimethyl formamide. The pH of the solution is adjusted to 8, and 2.25 g (5 mmoles) of Boc—Arg(NO$_2$)—OPfp are added. The solution is allowed to stand for one hour under maintaining its pH at the initial value, then diluted with 45 ml of chloroform and washed as described above. The solution is dried, evaporated, and the residue is treated with ethanol to obtain the protected heptapeptide ester. The product is obtained with a yield of 3.3 g (56% calculated for Thr, which corresponds to a yield of 91% in the individual steps); m.p.: 188°–193° C., $R_f^{(3)}=0.38$, $R_f^{(4)}=0.87$.

1.95 g of the above protected heptapeptide are dissolved in 10 ml of a 8 n hydrochloric acid solution in dioxane, and after 20 minutes of standing dry ether is added to the solution. The precipitated free heptapeptide hydrochloride, $R_f^{(4)}=0.20$, is filtered off, washed and dissolved in 15 ml of dimethyl formamide. The pH of the solution is adjusted to 8, and 0.87 g (2.25 mmoles) of Z—Sar—OPfp are added. The solution is allowed to stand for one hour under maintaining its pH at the initial value, then diluted with 45 ml of chloroform, washed successively with 10% aqueous citric acid solution, 1 n aqueous hydrochloric acid and water, dried and evaporated. The residue is triturated with ethanol, and the solid is filtered off and washed. 1.85 g (87%) of the protected octapeptide ester are obtained; m.p.: 202°–208° C., $R_f^{(3)}=0.20$, $R_f^{(4)}=0.86$.

STEP 2

Removal of the protecting groups 1.85 g (1.4 mmoles) of the protected octapeptide ester prepared as described in Step 1 of Example 4 are dissolved in 8 ml of dimethyl formamide, and 2.6 ml of 2-mercaptoethanol are added. The solution is stirred for one hour, and then the product is precipitated with dry ether. The resulting 1.6 g of the partially deprotected octapeptide free of dinitrophenyl group, $R_f^{(4)}=0.52$, is filtered off, washed, dissolved in 30 ml of a 5:1:1 mixture of methanol, acetic acid and water, and 1.0 g of a 10% palladium-on-carbon catalyst is added. Hydrogen is bubbled through the mixture for 30 hours under intense stirring, then the catalyst is filtered off and washed with the above solvent mixture. The filtrate is combined with the wash, evaporated to dryness, and the residue is treated with a 2:1 mixture of ether and ethanol. 0.98 g (83%) of the free octapeptide ester are obtained.

STEP 3

The crude free octapeptide ester is purified according to the general procedure given above. The resulting (sarcosine[1], threoinine/Me/methyl ester[8])-angiotensin-II has the following physical constants: Chromatographic characteristics: $R_f^{(6)}=0.29$, $R_f^{(8)}=0.55$, $R_f^{(9)}=0.27$. $E_{Glu}$ (pH=1.9). Amino acid analysis: His 1.03 (1), Arg 0.95 (1), Thr 0.93 (1), Pro 1.03 (1), Val 1.15 (1), Ile 1.03 (1), Tyr 0.90 (1), Sar 1.0 (1).

EXAMPLE 5

Preparation of (hydroxyacetic acid[1], threonine/Me/methyl ester[8])-angiotensin-II

STEP 1

Z—OGly—Arg(NO$_2$)—Val—Tyr(Bzl)—Ile—His(Dnp)—Pro—Thr(Me)—OMe 0.62 g (0.47 mmoles) of Boc—Arg(NO$_2$)—Val—Tyr(Bzl)—Ile—His(Dnp)—Pro—Thr(Me)—OMe, prepared as described in Step 1 of Example 4, are dissolved in 4 ml of a 8 n hydrochloric acid solution in dioxane. After 15 minutes of standing the free heptapeptide hydrochloride, $R_F^{(5)}=0.35$, is precipitated with dry ether, filtered off, washed and dissolved immediately in 10 ml of dimethyl formamide. The pH of the solution is adjusted to 8, and 0.8 g (2 mmoles) of Z—OGly—OPfp are added. The solution is allowed to stand for one hour under maintaining its pH at the initial value, then diluted with 30 ml of chloroform, and washed successively with 10% aqueous citric acid solution, 1 n aqueous hydrochloric acid and water. The solution is dried, evaporated, and the radius is treated with a 9:1 mixture of ether and ethanol. 0.60 g (90%) of the protected octapeptide ester are obtained; m.p.: 158°–162° C., $R_f^{(3)}=0.44$.

STEP 2

Removal of the protecting groups 0.6 g (0.42 mmoles) of the protected octapeptide ester prepared as described in Step 1 of Example 5 are dissolved in 2 ml of dimethyl formamide, and 1.2 ml of 2-mercaptoethanol are added. After one hour the partially deprotected octapeptide ester, free of dinitrophenyl group, is precipitated with dry ether. This substance is dissolved in methanol, the solution is decolourized, evaporated to dryness, and the residue is triturated with ether. 0.46 g of the partially deprotected octapeptide are obtained; $R_f^{(4)}=0.16$, $R_f^{(5)}=0.52$. This substance is dissolved in 25 ml of a 5:1:1 mixture of methanol, acetic acid and water, 0.3 g of a 10% palladium-on-carbon catalyst are added, and hydrogen is bubbled through the mixture for 17 hours under intense stirring. At the end of the reaction the catalyst is filtered off, washed with the above solvent mixture, the filtrate is combined with the wash and evaporated to dryness. Aqueous ethanol is added to the residue, the mixture is evaporated, and this operation is repeated several times. Finally the free octapeptide ester is triturated with ether and filtered off. 0.32 g (91%) of the product are obtained.

STEP 3

The free octapeptide ester is purified according to the general procedure described above. The physical constants of the product are as follows: Chromatographic characteristics: $R_f^{(7)}=0.22$, $R_f^{(8)}=0.73$, $R_f^{(9)}=0.56$. Amino acid analysis: Thr 0.92 (1), Pro 1.03 (1), Val 1.0 (1), Tyr 0.7 (1), His 1.0 (1), Arg 1.0 (1).

EXAMPLE 6

Preparation of (hydroxyacetic acid[1], threonine methyl ester[8])-angiotensin-II

STEP 1

Boc—Arg(NO$_2$)—Val—Tyr(Bzl)—Ile—His(Dnp)—Pro—Thr—OMe 3.8 g (20 mmoles) of Thr—OMe.HCl are dissolved in 50 ml of chloroform, and 2.8 ml (20 mmoles) of triethyl amine and 3.8 g (10 mmoles) of Boc—Pro—OPfp are added. The solution is allowed to stand for one hour under maintaining its pH at the initial value, then it is washed successively with 10% aqueous citric acid solution, 1 n aqueous hydrochloric acid and water, dried and evaporated. The resulting protected dipeptide ester, $R^{(3)}=0.77$, is dissolved in 20 ml of a 8 n hydrochloric acid solution in dioxane, and after 15 minutes of standing dry ether is added. The precipitated free dipeptide hydrochloride, $R_f^{(5)}=0.2$, is filtered off, washed and dissolved immediately in 30 ml of chloroform. The pH of the solution is adjusted to 8, and 4.7 g (8 mmoles) of Boc—His(Dnp)—OPfp are added. The solution is allowed to stand for one hour under maintaining its pH at the initial value, then washed successively with 10% aqueous citric acid solution, 1 n aqueous hydrochloric acid, 5% aqueous sodium hydrocarbonate solution and water, dried and evaporated. The resulting protected tripeptide ester, $R_f^{(3)}=0.47$, is dissolved in 20 ml of a 8 n hydrochloric acid solution in dioxane, and after 15 minutes of standing the free tripeptide ester hydrochloride is precipitated with dry ether. This substance, $R_f^{(5)}=0.23$, is dissolved immediately in 20 ml of a 5:1 mixture of chloroform and dimethyl formamide, the pH of the solution is adjusted to 8, and 4.0 g (10 mmoles) of Boc—Ile—OPfp are added. The solution is allowed to stand for one hour under maintaining its pH at the initial value, then washed successively with 10% aqueous citric acid solution, 5% aqueous sodium hydrocarbonate solution and water, dried and evaporated. The excess of the active ester is removed by repeatedly treating the residue with n-hexane. The resulting protected tetrapeptide, $R_f^{(3)}=0.45$, is dissolved in 15 ml of a 8 n hydrochloric acid solution in dioxane, and after 15 minutes of standing the free tetrapeptide ester hydrochloride, $R_f^{(5)}=0.25$, is precipitated with dry ether. This substance is dissolved immediately in 30 ml of dimethyl formamide, the pH of the solution is adjusted to 8, and 2.05 g (3.8 mmoles) of Boc—Tyr(Bzl)—OPfp are added. After 30 minutes of standing at the same pH value the soluton is evaporated, the residue is dissolved in ethyl acetate, 0.11 ml of N,N-dimethylamino-ethylamine are added to the solution, and after 15 minutes the mixture is washed as described above. The solution is dried, evaporated, the residue is triturated with dry ether, and the separated protected pentapeptide, $R_f^{(3)}=0.57$, is filtered off. This substance is dissolved in 10 ml of a 8 n hydrochloric acid solution in dioxane, and after 15 minutes of standing dry ether is added. The precipitated free pentapeptide ester hydrochloride, $R_f^{(5)}=0.27$, is filtered off, washed and dissolved immediately in 20 ml of dimethyl formamide. The pH of the solution is adjusted to 8, and 1.75 g (4.5 mmoles) of Boc—Val—OPfp are added. After one hour of standing at the same pH value the mixture is evaporated, the residue is dissolved in chloroform, and the solution is washed as described above. The solution is dried, evaporated, the oily residue is triturated with ether, and the separated protected hexapeptide, $R_f^{(3)}=0.55$, is filtered off and washed. This substance is dissolved in 8 ml of a 8 n hydrochloric acid solution is dioxane, and after 15 minutes of standing dry ether is added. The precipitated free hexapeptide ester hydrochloride, $R_f^{(5)}=0.23$, is filtered off, washed and dissolved immediately in 20 ml of dimethyl formamide. The pH of the solution is adjusted to 8, and 1.8 g (4 mmoles) of Boc—Arg(NO$_2$)—OPfp are added. After one hour of standing at the same pH the solvent is evaporated, the residue is dissolved in chloroform, and the solution is washed as described above. The solution is dried, evaporated, the residue is triturated with a 9:1 mixture of ether and ethanol, and the solid is filtered off and washed. 2.7 g (26% calculated for His; this corresponds to a yield of 80% in the individual steps) of the protected heptapeptide ester are obtained; m.p. 190°–195° C. (under decomposition), $R_f^{(4)}=0.47$.

STEP 2

Z—OGly—Arg(NO$_2$)—Val—Tyr(Bzl)—Ile—His(Dnp)—Pro—Thr—OMe 1.7 g (1.4 mmoles) of the protected heptapeptide prepared as described in Step 1 of Example 6 are dissolved in 10 ml of a 8 n hydrochloric acid solution in dioxane, and after 15 minutes of standing dry ether is added to the mixture. The precipitated free heptapeptide ester hydrochloride, $R_f^{(5)}=0.21$, is dissolved immediately in 20 ml of dimethyl formamide, the pH of the solution is adjusted to 8, and 0.82 g (2.1 mmoles) of Z—OGly—OPfp are added. The solution is allowed to stand for 30 minutes under maintaining its pH at the initial value, then diluted with 40 ml of chloroform, washed with 1 n aqueous hydrochloric acid and water, dried and evaporated. The residue is treated with dry ether to obtain 1.6 g (87%) of the protected octapeptide ester; $R_f^{(4)}=0.48$, m.p.: 188°–194° C.

STEP 3

Removal of the protecting groups 1.6 g (1.2 mmoles) of the protected octapeptide prepared as described in Step 2 of Example 6 are dissolved in 5 ml of dimethyl formamide, and 3.8 ml of 2-mercaptoethanol are added. After one hour of standing the octapeptide, free of dinitrophenyl group, is precipitated with dry ether, and purified by precipitation with ether from a methanolic solution. 1.3 g (94%) of the partially deprotected octapeptide are obtained; $R_f^{(4)}=0.35$, $R_f^{(5)}=0.72$. This substance is dissolved in 50 ml of a 5:1:1 mixture of methanol, acetic acid and water, 0.6 g of a 10% palladium-on-carbon catalyst are added, and hydrogen is bubbled through the mixture for 17 hours under intense stirring. At the end of the reaction the catalyst is filtered off, washed with the above solvent mixture, the filtrate is combined with the wash, and evaporated to dryness. Aqueous ethanol is added to the residue, the mixture is evaporated, and this operation is reported several times. Finally the residue is triturated with ether, and the free octapeptide is filtered off and washed. 0.064 g (92%) of the product are obtained.

STEP 4

The crude free octapeptide ester is purified according to the general procedure described above. The physical constants of the product are as follows: Chromatographic characteristics: $R_f^{(7)}=0.22$, $R_f^{(8)}=0.73$, $R_f^{(9)}=0.56$. Amino acid analysis: Thr 0.92 (1), Pro 1.03 (1), Val 1.0 (1), Ile 1.05 (1), Tyr 0.7 (1), His 1.0 (1), Arg 1.0 (1).

EXAMPLE 7

Preparaton of (sarcosine$^1$, alanine methyl ester$^8$)-angiotensin-II

STEP 1

Z—Sar—Arg(NO$_2$)—Val—Tyr(Bzl)—Ile—His(Dnp)—Pro—Ala—OMe 0.7 g (5 mmoles) of Ala—OMe.HCl are dissolved in 20 ml of chloroform, and 0.7 ml of triethyl amine and 1.14 g (3 mmoles) of Boc—Pro—OPfp are added. The mixture is allowed to stand for 30 minutes under maintaining its pH at the initial value, then washed successively with 10% aqueous citric acid, 1 n aqueous hydrochloric acid and water, dried and evaporated. The resulting protected dipeptide, $R_f^{(2)}=0.8$, is dissolved directly in 5 ml of a 8 n hydrochloric acid solution in dioxane, and after 10 minutes of standing the solution is diluted with dry ether and evaporated. The resulting free dipeptide hydrochloride, $R_f^{(5)}=0.32$, is dissolved in 20 ml of chloroform, the pH of the solution is adjusted to 8, and 2.7 g (4.5 mmoles) of Boc—His(Dnp)—OPfp are added. The solution is maintained at the same pH for one hour, and then 0.33 ml of dimethylamino-ethylamine are added. After 15 minutes the mixture is washed successively with 10% aqueous citric acid solution, 1 n aqueous hydrochloric acid, 5% aqueous sodium hydrocarbonate solution and water, dried and evaporated. The resulting protected tripeptide, $R_f^{(2)}=0.27$, is dissolved in 10 ml of a 8 n hydrochloric acid solution in dioxane, and after 15 minutes of standing the product is precipitated with dry ether. The free tripeptide hydrochloride, $R_f^{(5)}=0.48$, is filtered off, washed and dissolved immediately in 30 ml of a 2:1 mixture of chloroform and dimethyl formamide. The pH of the solution is adjusted to 8, and 2.4 g (6 mmoles) of Boc—Ile—OPfp are added. After 30 minutes of standing at the same pH value the solvent is evaporated, the residue is dissolved in ethyl acetate, the solution is washed as described above, dried and evaporated. The residue is triturated with a 1:9 mixture of ether and n-hexane, and the isolated protected tetrapeptide, $R_f^{(2)}=0.29$, is dissolved in 10 ml of a 8 n hydrochloric acid solution in dioxane. After 10 minutes the free tetrapeptide hydrochloride, $R_f^{(5)}=0.67$, is precipitated with dry ether, washed and dissolved immediately in 30 ml of a 2:1 mixture of chloroform and dimethyl formamide. The pH of the solution is adjusted to 8, and 1.78 g (3.3 mmoles) of Boc—Tyr(Bzl)—OPfp are added. The solution is maintained at the same pH value for 15 minutes, the the solvent is evaporated, the residue is dissolved in ethyl acetate, and the solution is washed as described above. The protected pentapeptide hydrochloride, $R_f^{(4)}=0.35$, is isolated by treatment with dry ether, dissolved in 10 ml of a 8 n hydrochloric acid solution in dioxane, and the free pentapeptide hydrochloride, $R_f^{(4)}=0.35$, is precipitated with dry ether. The substance is filtered off and dissolved immediately in 20 ml of dimethyl formamide. The pH of the solution is adjusted to 8, and 1.55 g (4 mmoles) of Boc—Val—OPfp are added. The mixture is maintained at the same pH value for 30 minutes, thereafter the solvent is evaporated, the residue is dissolved in chloroform, the solution is washed as described above, dried and evaporated. The protected hexapeptide, $R_f^{(2)}=0.35$, is isolated by triturating the residue with dry ether. The substance is dissolved in 8 ml of a 8 n hydrochloric acid solution is dioxane, and after 20 minutes of standing the free hexapeptide hydrochloride, $R_f(5)=0.75$, is precipitated with dry ether. The product is filtered off, washed, and dissolved immediately in 20 ml of dimethyl formamide. The pH of the solution is adjusted to 8, and 2.64 g (6 mmoles) of Boc—Arg(NO$_2$-)—OPfp are added. The mixture is allowed to stand for one hour under maintaining its pH at the initial value, then diluted with 60 ml of chloroform, washed with 1 n aqueous hydrochloric acid and water, dried and evaporated. The resulting protected heptapeptide, $R_f(4)=0.85$, is triturated with a 1:3 mixture of ethanol and ether, filtered off, washed and dissolved in 10 ml of a 8 n hydrochloric acid solution in dioxane. The free heptapeptide hydrochloride, $R_f(4)=0.15$, is precipitated with dry ether, filtered off, washed, and dissolved immediately in 20 ml of dimethyl formamide. The pH of the solution is adjusted to 8, and 1.27 g (3.3 mmoles) of Z—Sar—OPfp are added. The solution is maintained at the same pH value for 15 minutes, then diluted with 60 ml of chloroform, washed as described above, dried and evaporated. The residue is triturated with 25 ml of ethanol, and the separated solid is filtered off and washed. 1.37 g (33% calculated for Pro; this corresponds to a yield of 86% in the individual steps) of the protected octapeptide ester are obtained; m.p.: 192°–196° C., $R_f(4)=0.70$.

STEP 2

Removal of the protecting groups 1.37 g (1 mmole) of the protected octapeptide ester prepared as described in Step 1 of Example 7 are dissolved in 3 ml of dimethyl formamide, and 1.9 ml of 2-mercaptoethanol are added. After one hour the peptide free from dinitrophenyl group is precipitated with dry ether, filtered off and washed. The resulting 1.2 g (99%) of partially deprotected product, $R_f(4)=0.20$, is dissolved in 20 ml of a 5:1:1 mixture of methanol, acetic acid and water, 0.6 g of a 10% palladium-on-carbon catalyst are added to the solution, and hydrogen is bubbled through the mixture for 20 hours under intense stirring. At the end of the reaction the catalyst is filtered off, washed with the above solvent mixture, the filtrate is combined with the wash, and evaporated to dryness. Aqueous ethanol is added to the residue, the mixture is evaporated, and this operation is repeated several times. Finally the residue is triturated with a 1:1 mixture of ethanol and ether to obtain 0.7 g (75%) of the free octapeptide ester.

STEP 3

The crude octapeptide ester is purified according to the general procedure described above. The physical constants of the product are as follows: Chromatographic characteristics: $R_f(7)=0.23$, $R_f(8)=0.54$, $R_f(9)=0.27$. Amino acid analysis: His 0.97 (1), Arg 1.03 (1), Pro 1.06 (1), Val 1.03 (1), Ile 0.98 (1), Tyr 0.6 (1), Sar 1.0 (1).

What we claim is:

1. A compound of the formula (I)

$$X-Arg-Val-Tyr-Ile-His-Pro-Ile-OA \quad (I)$$

wherein

X is L-Sarcosyl or hydroxyacetyl and

A is a $C_1$–$C_5$ alkyl group, or a pharmaceutically acceptable acid addition salt or complex thereof.

2. L-Sarcosyl-L-arginyl-L-valyl-L-tyrosyl-L-isoleucyl-L-histidyl-L-prolyl-L-isoleucine methyl ester as defined in claim 1.

3. Hydroxy-acetyl-L-arginyl-L-valyl-L-tyrosyl-L-isoleucyl-L-histidyl-L-prolyl-L-isoleucine methyl ester as defined in claim 1.

4. An antihypertensive composition which comprises a pharmaceutically effective amount of the compound of the formula (I) as defined in claim 1, or a pharmaceutically acceptable acid addition salt or complex thereof in combination with a pharmaceutical excipient.

5. A method of treating hypertension in a susceptible animal subject which comprises the step of administering to said animal subject a pharmaceutically effective amount of the compound of the formula (I) as defined in claim 1, or a pharmaceutically acceptable acid addition salt or complex thereof.

* * * * *